United States Patent [19]

Kubota et al.

[11] 3,984,378
[45] Oct. 5, 1976

[54] PROCESS FOR MANUFACTURING NITROPYRENE-FORMALDEHYDE RESIN

[75] Inventors: Tomio Kubota; Shoji Maruyama; Takao Igawa, all of Tokyo, Japan

[73] Assignee: Kabushiki Kaisha Ricoh, Tokyo, Japan

[22] Filed: Mar. 12, 1974

[21] Appl. No.: 450,428

[30] Foreign Application Priority Data
  Mar. 12, 1973 Japan............................ 48-029217
  Mar. 12, 1973 Japan............................ 48-037262

[52] U.S. Cl............................ 260/67 A; 96/1.5; 96/1.6; 260/30.4 R; 260/30.8 R; 260/31.2 R; 260/31.8 R; 252/501
[51] Int. Cl.².......................................... C08G 10/02
[58] Field of Search........ 260/67 A, 30.4 R, 31.2 R, 260/30.8 R, 31.8 R, 93.5 R

[56] References Cited
UNITED STATES PATENTS 3,740,218  6/1973  Contois et al................. 260/67 A X
3,842,038  10/1974  Löhr et al........................ 260/67 A

*Primary Examiner*—Lucille M. Phynes
*Attorney, Agent, or Firm*—Cooper, Dunham, Clark, Griffin & Moran

[57] ABSTRACT

Photoconductive, film forming nitropyrene-formaldehyde resins characterized by a repeating structural unit of the formula:

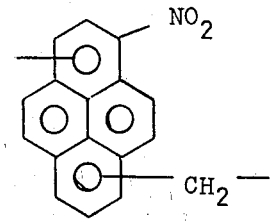

and process for preparation, the photoconductive films themselves, and such films on an electrically conductive support.

8 Claims, 1 Drawing Figure

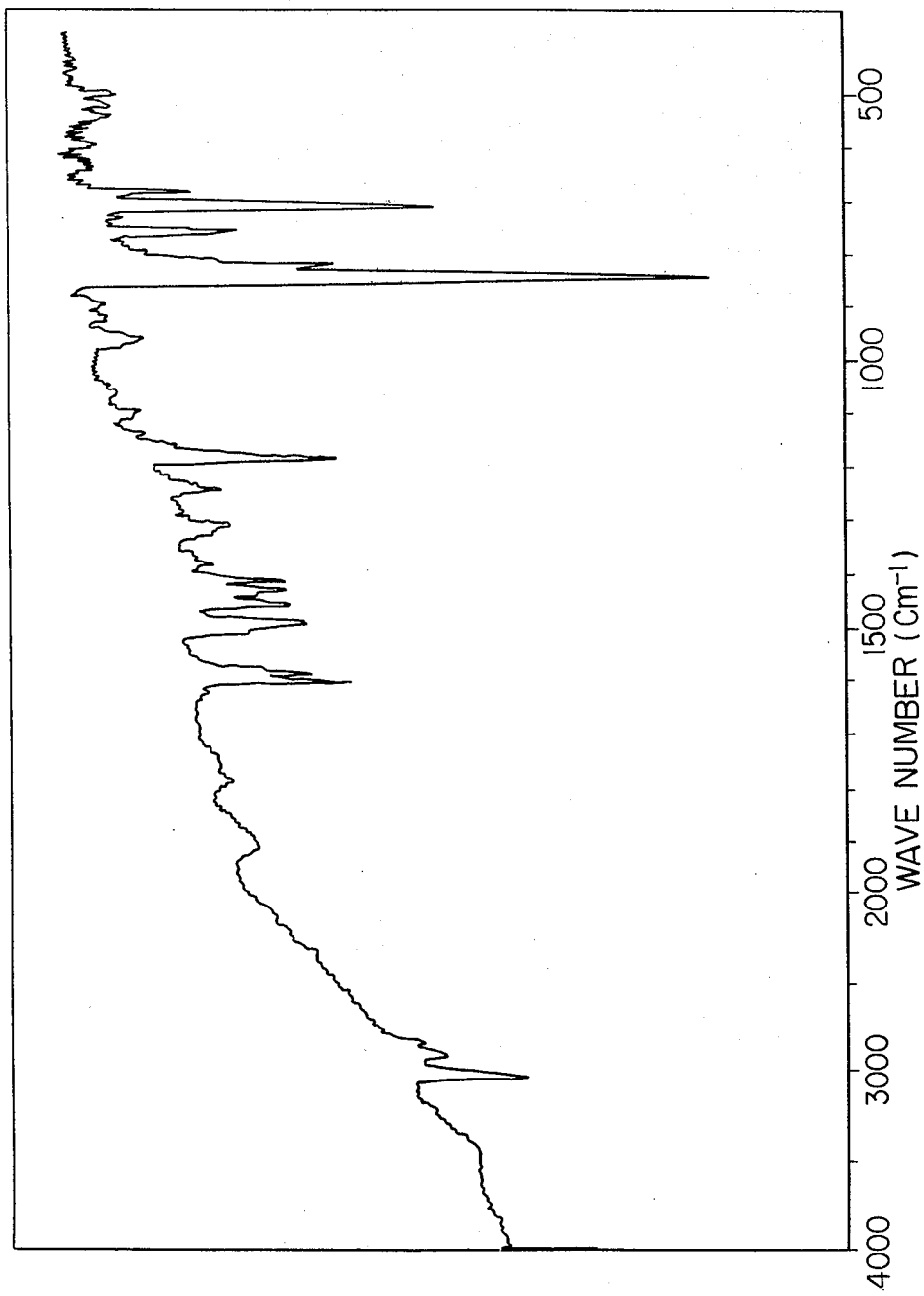

PROCESS FOR MANUFACTURING NITROPYRENE-FORMALDEHYDE RESIN

BACKGROUND OF THE INVENTION a. Field of the Invention

The invention relates to photoconductive film forming nitropyrene-formaldehyde resins, processes for producing such resins, and photoconductive films prepared from such resins.

b. Description of the Prior Art

A variety of organic photoconductors are known. Of these, poly-N-vinyl carbazole is the most widely employed, although others such as N-alkyl derivatives of poly-N-vinyl carbazole, anthracene, perylene, and various derivatives of acylhydrazones, oxadiazoles, triazoles, pyrazolines, imidazolones, benzimidazoles, benzoxazoles and benzothiazoles have also been described. Some organic photoconductors are readily deposited from a solvent in the form of a film. Others are not so readily deposited. Among those organic photoconductors which do not have satisfactory film forming properties, there are included bromopyrene-formaldehyde resins such as disclosed in Aktuelle Probleme Der Electrophotographie, 3 Europaishes Kolloquium, Aug., 1971. These resins, moreover, do not form a good adhesive bond on the support. As a result, it has not been possible to take full advantage of the photoconductivity of the resins. The addition of plasticizers to improve the film forming characteristics of the base resin, or the admixture of the base resin with other more adhesive resins to improve the adhesive quality of the base resin, has not produced satisfactory results. In both cases, the additives adversely affect the photoconductivity of the base resin.

Organic photoconductors are generally superior to inorganic photoconductors because they are lighter, and because they manifest greater flexibility, light transmission and homogeneity. Because of these improved properties, unsupported films of photoconductive materials are useful as second originals in diazo copying systems, and in electrophotographic machines employing belt type photosensitive materials.

SUMMARY OF THE INVENTION

The present invention provides novel photoconductive nitropyrene-formaldehyde resins, and processes for their manufacture. These resins are far superior to the aforementioned bromopyrene-formaldehyde resins in film forming and adhesive properties. They are, moreover, superior in compatability with conventional additives, of good sensitivity, and possess other properties which achieve the wide range of practical requirements of the copying field.

BRIEF DESCRIPTION OF THE DRAWING

The accompanying drawing is an infrared curve of nitropyrene-formaldehyde resins of the invention.

DETAILED DESCRIPTION OF THE INVENTION

The products of this invention are photoconductive, film forming resins characterized by repeating structural units of the formula:

They are produced by a condensation reaction between nitropyrene and formaldehyde, suitably in the form of paraformaldehyde.

The starting material, nitropyrene utilized in the present invention is known and can be readily prepared. One suitable process is described in PB Report (L 73377, pp. 2271~ 2272) or Ann. 531 107 (1937). It can be prepared, for example, by reacting pyrene with either nitric acid (concentration: 22%) or a mixture of dilute nitric acid (D=1.4) and acetic acid.

The condensation is preferably carried out in a reaction inert, polar organic solvent. Any of a large number of solvents may be employed. The preferred solvents from the aspect of economy and yield are tetrahydrofuran, chlorobenzene and glacial acetic acid.

The reaction temperature is not critical, and may vary from room temperature or below (about 20° C.) to as high as 100° C. or even higher.

The presence of a catalyst in the reaction system may help to increase the rate and yield of the reaction. Both acid and alkaline catalysts may be used. Typical catalysts which are mentioned by way of example include inorganic acids such as sulfuric acid, hydrochloric acid, and phosphoric acid (polyphosphoric acid), organic acids such as phthalic acid, Lewis acid such as zinc chloride ($ZnCl_2$), and alkaline substances such as sodium hydroxide, potassium hydroxide and organic amine compounds.

The preferred combination of solvent and catalyst for use in this invention is glacial acetic acid and zinc chloride. This combination has been observed to give excellent yields under the most economic conditions.

The resins of the invention are more precisely represented by the formula:

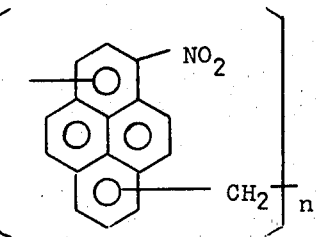

wherein $n$ is an integer.

The numerical value of $n$ in the products of this invention is such that the molecular weight of the product is in the film forming range. The structure of the products is quite complex, and apparently involves both two and three dimensional bonding. It is presently believed, however, that for film forming resins the value of $n$ is from about 2 to 6, although it may be appreciably higher.

The photoconductive films of this invention will contain a resin of the invention as the principal photoconductive component. However, other additives may be employed. These would include, for example, other organic or inorganic photoconductors; plasticizers such as polyester resin, polycarbonate, diphenyl chloride, urethan resin, epoxy resin, maleic acid resin, alkyd resin, polyvinyl acetate, polyvinyl ether etc.; and sensitizers.

Sensitizers utilized in this invention include not only pigment and dye sensitizers but also all of those substances which are known as the electron acceptor; for instance, benzopyrylium salt e.g., salts which are disclosed in the specification of Japanese Patent Appln. No. 106050/1970
Japanese Patent Appln. No. 106564/1970
Japanese Patent Appln. No. 118105/1970
Japanese Patent Appln. No. 125983/1970 and
Japanese Patent Appln. No. 130215/1970 pyronyl-benzopyrylium-containing materials such as disclosed in the specification of Japanese Patent Appln. No. 100799/1972
Japanese Patent Appln. No. 100800/1972 and
Japanese Patent Appln. No. 100801/1972, Rose Bengal, Nile Blue, Methyl Violet, Rhodamine 6B and other conventional sensitizers, such as the dyes and pigments disclosed in the literature, for example by Hayashi et al, Bull. Chem. Soc. Japan 39 1660 (1966). Typically useful electron acceptors include 2,4,7-trinitro-9-fluorenone, 2,7-dinitro-9-dicyanomethylene fluorene, 2,5-dinitro-9-dicyanomethylene fluorene, 2,6-dinitro-9-dicyanomethylene fluorene, 2-aza-9-fluorenone, mononitro-2-aza-9-fluorenone, mononitro-9-dicyanomethylene-2-azafluorene, 2,6,8-trinitro-4H-indeno-[1,2-B]-thiophene-4-on, 6,8-dinitro-4-dicyanomethylene-4H-indeno-[1,2-B]-thiophene, phenanthrene-quinone nitro compound, tetracyanoethylene, tetracyanodimethane, bromenil, chloranil, benzoquinone, naphthaquinone, anthraquinone derivative, phthalic anhydride, picric acid, trichloroacetic acid, etc.

Useful electron acceptors also include any of those substances disclosed in literature, for example, by S. Oka, K. Mori, S. Kusabayashi, Y. Taniguchi, Y. Yamamoto, S. Ishiguro, R. Mitsukawa in "Electrophotograph" 5 19 (1964 and H. Hoegl "J. Phys. Chem.", 69 755 (1965) is applicable.

Photosensitive materials for use in electrophotography in accordance with this invention are prepared in a conventional manner, for example a nitropyrene-formaldehyde resin with at least one sensitizer in the ratio of 1 mol of monomeric unit of the former to $1 \times 10^{-6}$ mol~2 mols — preferably $1.5 \times 10^{-5}$ mol in order to satisfy both the sensitization effect and the photoconductivity — of the latter, either dissolving or dispersing the resulting mixture in a proper organic solvent such as tetrahydrofuran, chlorobenzene, toluene, dichloroethane, etc. or adding a small quantity of organic solvent to said mixture, and applying the thus obtained solution or dispersion onto the surface of a conductive support by coating with a doctor blade, wire bar and the like or coating with a test coating machine, followed by drying, thereby forming a photoconductive layer having a thickness preferably in the range of 1~30 $\mu$ on said support.

Useful electrically conductive supports for use in this invention include metal plates such as copper and aluminium; paper or polymeric films suitably treated for conductivity; and glass or paper surface coated with a metal or metal oxide or halogenide through vacuum evaporation.

The products of this invention have excellent photoconductivity, as well as superior film forming and adhesive properties. These last two properties can be improved by mixing with at least one additive reinforcing agent, such as diphenyl chloride, polyvinyl acetate, polyvinyl acetal, polyvinyl ether, polyester-containing plasticizer, etc. The range of useful weight ratios of additive reinforcing agent to resin is from about 1~50 parts by weight of the former to 100 parts by weight of the latter, i.e. 1:100 to 50:100. However appreciable variation can be tolerated.

Electrophotographic copying utilizing the products of the present invention is conducted in a conventional manner. In other words, a reproduction faithful to an original image can be obtained by known electrophotographic methods including xerography — through the process comprising electrifying the photosensitive material by corona discharge, forming an electrostatic latent image by exposing the thus electrified photosensitive material to an appropriate light source, developing the thus formed latent image with a liquid or powder developer, transferring the developed image onto a transfer paper, if necessary, and fixing. If unused particles of developer remain on the photosensitive material after use, they can be removed by cleaning and thereafter reclaimed.

The resins of this invention can also be prepared by direct nitration of pyrene-formaldehyde resins produced by condensation of pyrene and a form of formaldehyde.

The following non-limiting examples are given by way of illustration only:

EXAMPLE 1

Synthesis of Nitropyrene

A mixture prepared by thoroughly pulverizing 10 g of pyrene in a mortar and adding 40.5 g of 22% nitric acid was stirred for 8 hours at a temperature in the range of 40°~45° C. The resulting reaction product was washed in a wash liquid until it becomes neutral, and was then dried. By employing about 250 ml of ethyl alcohol and repeating recrystallization of the crude nitropyrene three times, 2.5 g of crystals were produced. The melting point of this nitropyrene was in the range of 153°~154° C. The results of elemental analysis are:

Calculated value (as $C_{16}H_9O_2N$): C: 77.73%, H: 3.64%, N: 5.67%. Actual value: C: 77.25%, H: 3.72%, N: 5.43%.

EXAMPLE 2

Synthesis of Nitropyrene-formaldehyde Resin

A mixture prepared by adding 250 ml of glacial acetic acid to 7.1 g of nitropyrene produced as above was heated at a temperature in the range of 95°~100° C. to dissolve the nitropyrene completely. Subsequently, upon adding 1.3 g of paraformaldehyde and 6 g of zinc chloride thereto, the resulting solution was subjected to 4 hours' vigorous stirring, followed by cooling, suction filtration, thorough washing in a water-methyl alcohol mixture solvent and drying, whereby 5 g of crystals were produced. The thus produced crystals were dissolved in about 70 ml of tetrahydrofuran, and the resulting solution was added dropwise to 300 ml of methanol and filtered with suction. The precipitate was dried to provide 3.5 g of crystalline nitropyrene-formaldehyde resin. The melting point of this product was found to be in the range of 198°~200° C. The infrared curve of this product is shown in the figure. The curve shows absorption of 1430 cm$^{-1}$ and 1460 cm$^{-1}$ which are characteristics of the aromatic nucleus, and at 1380 cm$^{-1}$ which is characteristic of the methylene group, 1330 cm$^{-1}$, 1590 cm$^{-1}$ and 845 cm$^{-1}$ which are characteristic of a nitro group attached to a carbon atom. Further, the result of elemental analysis on the basis of a molecular weight of $C_{17}H_{10}NO_2=259$ for the monomeric unit was as follows:

Calculated value: C: 78.76%, H: 3.47%, N: 5.41%. Actual value: C: 78.93%, H: 3.78%, N: 5.05%.

EXAMPLE 3

Synthesis of Nitropyrene

A solution was prepared by dissolving 101 g of pyrene in 800 ml of glacial acetic acid. While heating this solution at 50° C. in water bath with stirring, a mixed solution of 42 ml of nitric acid (D=1.4) and 50 ml of glacial acetic acid was slowly added thereto dropwise. At the end of 30 minutes, the reacted mixture was filtered with suction. The precipitate was washed with a small quantity of glacial acetic acid and then thoroughly washed with water to obtain 115 g of yellow crystals (melting point: 150° C.). By recrystallizing these crystals in glacial acetic acid, crystals having a melting point in the range of 153°~154° C. were obtained. The result of elemental analysis of this product was as shown in the following table:

Calculated value (as $C_{16}H_9O_2N$): C: 77.73%, H: 3.64%, N: 5.67%. Actual value: C: 77.41%, H: 3.80%, N: 5.53%.

EXAMPLE 4

Synthesis of Nitropyrene-formaldehyde Resin

A mixture containing 250 ml of glacial acetic acid and 7.1 g of nitropyrene produced as above was heated at a temperature in the range of 95°~100° C., thereby dissolving nitropyrene completely. Subsequently, upon adding 1.3 g of paraformaldehyde and 8 g of zinc chloride, the resulting solution was subjected to 4 hours' vigorous stirring, followed by the same operation as in Example 2. As a result, 3.85 g of crystalline nitropyrene-formaldehyde resin were obtained. The melting point and the infrared absorption curve of this resin were substantially the same as that of the resin obtained in Example 2.

EXAMPLE 5

A solution prepared by dissolving 0.433 g of nitropyrene-formaldehyde resin obtained as in the foregoing examples and 0.053 g 2,7-dinitro-9-dicyanomethylene fluorene in 3 g of tetrahydrofuran was coated to the extent of 6~7 $\mu$ in dry thickness by means of a doctor blade adjusted to hold a gap of 7.5~8 mils on a conductive support consisting of a polyester film coated with aluminum by vacuum evaporation.

After impressing negative electricity by corona discharge of about 6 KV on the photoconductive layer of the thus obtained photosensitive material and subsequently applying an incandescent light having the illumination of 20 luxes thereto, the degree of exposure E ½ (lux.sec.) required for the decay of the sensitivity or the surface potential thereto to half and the degree of exposure E 1/5 (lux.sec.) required for the decay of same to one fifth were measured.

Further, after impressing the same photosensitive material with negative electricity by corona discharge of about 6 KV by the use of a commercial electrophotographic copying machine, by applying an image light having the illumination of 20 lux.sec. by means of a tungsten lamp to the thus electrified material and dipping it in a commercial liquid developer for use in electrophotography subsequent thereto, a copied image reproducing the original image faithfully was obtained.

EXAMPLE 6

A solution prepared by dissolving 0.433 g of nitropyrene-formaldehyde resin obtained as above and 0.044 g of mononitro-9-dicyanomethylene-2-azafluorene in 3 g of tetrahydrofuran was coated to the extent of 6~7 $\mu$ in dry thickness by means of a doctor blade adjusted to hold a gap of 7.5~8 mils on a support consisting of a polyester film coated with aluminum by vacuum evaporation, whereby a photoconductive layer was formed on said support.

After impressing negative electricity by corona discharge of about 6 KV on the photoconductive layer of the thus obtained photosensitive material and subsequently applying an incandescent light having the illumination of 20 luxes thereto, the degree of exposure E ½ (lux.sec.) required for the decay of the surface potential thereof to half and the degree of exposure E 1/5 (lux.sec.) required for the decay of same to one fifth were measured.

Further, after impressing the same photosensitive material with negative electrically by corona discharge of about 6 KV by the use of a commercial electrophotographic copying machine, by applying an image light having the illumination of 20 lux.sec. by means of a tungsten lamp to the thus electrified material and dipping it in a commercial liquid developer for use in electrophotography subsequent thereto, a copied image reproducing the original image faithfully was obtained.

EXAMPLE 7

A solution prepared by dissolving 0.433 g of nitropyrene-formaldehyde resin obtained as above and 0.530 g of 2,4-diniro-9-dicyanomethylene fluorene in 3 g of tetrahydrofuran was coated to the extent of 6~7 $\mu$ in dry thickness by means of a doctor blade adjusted to hold a gap of 7.5~8 mils on a support consisting of a polyester film coated with aluminum by vacuum evaporation, whereby a photoconductive layer was formed on said support.

After impressing negative electricity by corona discharge of about 6 KV on the photoconductive layer of the thus obtained photosensitive material and subsequently applying an incandescent light having the illumination of 20 luxes thereto, the degree of exposure E ½ (Lux.sec.) required for the decay of the surface potential thereof to half and the degree of exposure E 1/5 (lux.sec.) required for the decay of same to one fifth were measured.

Further, after impressing the same photosensitive material with negative electricity by corona discharge of about 6 KV by the use of a commercial electrophotographic copying machine, by applying an image light having the illumination of 20 lux.sec. by means of a tungsten lamp to the thus electrified material and dipping it in a commercial liquid developer for use in electrophotography subsequent thereto, a copied image reproducing the original image faithfully was obtained.

EXAMPLE 8

A solution prepared by dissolving 0.433 g of nitropyrene-formaldehyde resin obtained as above, 0.053 g of 2,7-dinitro-9-dicyanomethylene fluorene, 2.5 g of tetrahydrofuran solution of 10% polyester Adhesive 49000 (the trade name of a polyester resin manufactured by E. I. DuPont, Inc.) and 0.025 g of tetrahydrofuran solution of 10% silicone oil AK-1000 (the trade name of a silicone oil manufactured by Worker Chem. GMBH) in 3.00 g of tetrahydrofuran was coated to the extent of 6~7 μ in dry thickness by means of a doctor blade adjusted to hold a gap of 7.5~8 mils on a support consisting of a polyester film coated with aluminum by vacuum evaporation, whereby a photosensitive layer was formed on said support.

After impressing negative electricity by corona discharge of about 6 KV on the photoconductive layer of the thus obtained photosensitive material and subsequently applying an incandescent light having the illumination of 20 luxes thereto, the degree of exposure E ½ (lux.sec.) required for the decay of the surface potential thereof to half and the degree of exposure E 1/5 (lux.sec.) required for the decay of same to one fifth were measured.

Further, after impressing the same photosensitive material with negative electricity by corona discharge of about 6 KV by the use of a commercial electrophotographic copying machine, by applying an image light having the illumination of 20 lux.sec. by means of a tungsten lamp to the thus electrified material and dipping it in a commercial liquid developer for use in electrophotography subsequent thereto, a copied image reproducing the original image faithfully was obtained.

EXAMPLE 9

A solution prepared by dissolving 0.433 g of nitropyrene-formaldehyde resin obtained in the foregoing examples of synthesis, 0.053 g of 2,4,7-trinitro-9-fluorenone, 2.5 g of tetrahydrofuran solution of 10% polyester Adhesive 49000 and 0.025 g of tetrahydrofuran solution of 10% silicone oil AK-1000 in 3.00 g of tetrahydrofuran was coated to the extent of 6~7 μ in dry thickness by means of a doctor blade adjusted to hold a gap of 7.5~8 mils on a support consisting of a polyester film coated with aluminum by vacuum evaporation, whereby a photoconductive layer was formed on said support.

After impressing negative electricity by corona discharge of about 6 KV on the photoconductive layer of the thus obtained photosensitive material and subsequently applying an incandescent light having the illumination of 20 luxes thereto, the degree of exposure E ½ (lux.sec.) required for the decay of the surface potential thereof to half and the degree of exposure E 1/5 (lux.sec.) required for the decay of same to one fifth were measured.

Further, after impressing the same photosensitive material with negative electricity by corona discharge of about 6 KV by the use of a commercial electrophotographic copying machine, by applying an image light having the illumination of 20 lux.sec. by means of a tungsten lamp to the thus electrified material and dipping it in a commercial liquid developer for use in electrophotography subsequent thereof, a copied image reproducing the original image faithfully was obtained.

The results of measurement of E ½ (lux.sec.) and E 1/5 (lux.sec.) in the above Examples 5 through 9 are shown in the following table. For comparison, the results of measurement of E ½ (lux.sec.) and E 1/5 (lux.-sec.) of photosensitive materials prepared by processing bromopyrene-formaldehyde are also shown in the same table.

| Resin (molar ratio) | Electron Acceptor (molar ratio) | Adhesive or Plasticizer | E 1/2 lux.sec. | E 1/5 lux.sec. |
|---|---|---|---|---|
| Bromopyrene-formaldehyde (1) | None | None[1] | — | — |
| Nitropyrene-formaldehyde (1) | None | None | 73.1 | — |
| Bromopyrene-formaldehyde (1) | D.D.F (0.1) | None[1] | — | — |
| Nitropyrene-formaldehyde (1) | D.D.F (0.1) | None | 13.1 | 50.9 |
| Bromopyrene-formaldehyde (1) | D.D.F (0.1) | Present[2] | 14.9 | 62.9 |
| Nitropyrene-formaldehyde (1) | D.D.F (0.1) | Present[2] | 14.9 | 55.4 |
| Nitropyrene-formaldehyde (1) | N.D.A.F (0.1) | None | 18.4 | 79.8 |
| Bromopyrene-formaldehyde (1) | N.D.A.F (0.1) | None[1] | — | — |
| Nitropyrene-formaldehyde (1) | D.D.F (1) | None | 9.1 | 28.6 |
| Nitropyrene-formaldehyde (1) | T.N.F (0.1) | None | 48.0 | — |
| Bromopyrene-formaldehyde (1) | T.N.F (0.1) | None[1] | — | — |

D.D.F: 2,7-dinitro-9-dicyanomethylene fluorene
N.D.A.F: mononitro-9-dicyanomethylene-2-azafluorene
T.N.F: 2,4,7-trinitro-9-fluorenone
[1]Because of the absence of adhesive or plasticizer, it was impossible to form a film.
[2]The plasticizer was polycarbonate.

It will be clear from the results reported above that the resins of this invention are much superior to results which can be obtained with bromopyrene-formaldehyde resins.

The above table shows that nitropyrene-formaldehyde has better characteristics in E 1/5 than bromopyrene-formaldehyde. Therefore when a image is produced on the photosensitive material, the background density is low.

Since the solubility of nitropyrene-formaldehyde to solvent and compatibility with resins are better, it is possible to add 1 mole of electron acceptor to 1 mole of monomer unit of nitropyrene-formaldehyde, so that this gives about two times better sensitivity than the photosensitive material based on bromopyrene-formaldehyde (Item 9 in the above Table) Also this fact is good for the exposing, charging process, etc. as well as image characteristics.

While when 1 mole of monomer unit of bromopyrene-formaldehyde and the same amount of electron acceptor are mixed to make a photosensitive material, crystals are formed owning to the poor solubility of bromopyrene-formaldehyde to the solvent. And a usable photosensitive material is not obtained.

What is claimed is:

1. A photoconductive, film forming resin wherein the repeating structural unit is of the formula:

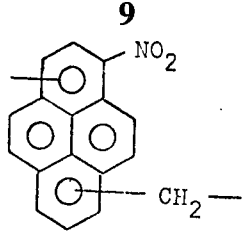

2. A photoconductive resin of the formula:

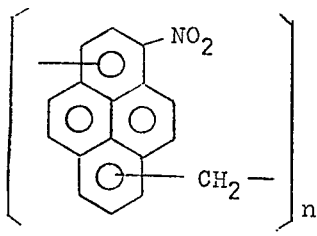

wherein $n$ is from 2 to 6.

3. A photoconductive film comprising as the principal photoconductive component a resin wherein the repeating structural unit is of the formula:

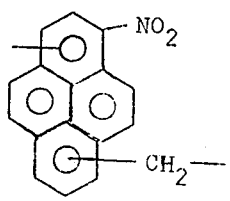

4. A photoconductive film comprising as the principal photoconductive component a resin of the formula:

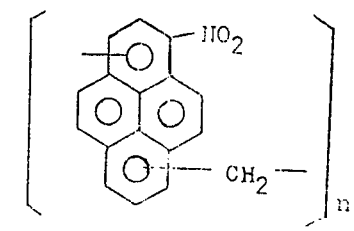

wherein $n$ is from 2 to 6.

5. A process for producing a photoconductive, film forming resin wherein the repeating structural unit is represented by the formula:

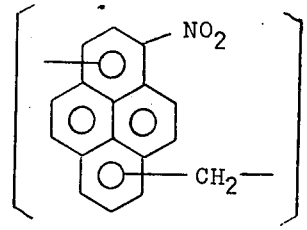

which comprises condensation polymerization of nitropyrene and paraformaldehyde.

6. A process as in claim 5, wherein the condensation reaction is carried out in a solvent selected from the group consisting of tetrahydrofuran, chlorobenzene and glacial acetic acid.

7. A process as in claim 5 employing a catalyst selected from the group consisting of sulfuric acid, hydrochloric acid, phosphoric acid, phthalic acid, zinc chloride, sodium hydroxide, potassium hydroxide and organic amines.

8. A process as in claim 5, wherein the condensation reaction is carried out in glacial acetic acid employing zinc chloride as a catalyst.

* * * * *